United States Patent
Azad et al.

(10) Patent No.: US 9,146,226 B1
(45) Date of Patent: Sep. 29, 2015

(54) METHODS AND DEVICES FOR DETECTING UNSATURATED COMPOUNDS

(75) Inventors: Abdul-Majeed Azad, Perrysburg, OH (US); Desikan Sundararajan, Maumee, OH (US); Robert Howard Kinner, Mentor, OH (US)

(73) Assignee: The University of Toledo, Toledo, OH (US)

( * ) Notice: Subject to any disclaimer, the term of this patent is extended or adjusted under 35 U.S.C. 154(b) by 100 days.

(21) Appl. No.: 13/482,532

(22) Filed: May 29, 2012

Related U.S. Application Data

(60) Provisional application No. 61/490,395, filed on May 26, 2011.

(51) Int. Cl.
| | |
|---|---|
| *G01N 33/28* | (2006.01) |
| *G01N 21/33* | (2006.01) |
| *G01N 33/543* | (2006.01) |
| *G01N 27/403* | (2006.01) |
| *G01N 27/327* | (2006.01) |

(52) U.S. Cl.
CPC ............ *G01N 33/2835* (2013.01); *G01N 21/33* (2013.01); *G01N 27/3271* (2013.01); *G01N 27/403* (2013.01); *G01N 33/5438* (2013.01)

(58) Field of Classification Search
CPC .............. G01N 21/33; G01N 33/2835; G01N 33/5438; G01N 27/403; G01N 27/3271
USPC .......................... 436/142, 149; 422/98, 82.01
See application file for complete search history.

(56) References Cited

U.S. PATENT DOCUMENTS

| | | |
|---|---|---|
| 4,142,400 A | 3/1979 | Colla et al. |
| 4,236,307 A | 12/1980 | Colla et al. |
| 4,410,632 A | 10/1983 | Dilley et al. |
| 4,414,839 A | 11/1983 | Dilley et al. |
| 4,581,204 A | 4/1986 | Voit |
| 4,631,952 A | 12/1986 | Donaghey |
| 4,644,333 A | 2/1987 | Barendsz et al. |
| 4,674,320 A | 6/1987 | Hirschfeld |
| 4,822,465 A | 4/1989 | Jones et al. |
| 4,836,012 A | 6/1989 | Doty et al. |
| 5,047,214 A | 9/1991 | Fukui et al. |
| 5,215,643 A | 6/1993 | Kusanagi et al. |
| 5,322,602 A | 6/1994 | Razaq |
| 5,417,100 A | 5/1995 | Miller et al. |
| 5,417,821 A | 5/1995 | Pyke |
| 5,425,869 A | 6/1995 | Noding et al. |
| 5,536,473 A | 7/1996 | Monkman et al. |
| 5,591,321 A | 1/1997 | Pyke |
| 5,788,833 A | 8/1998 | Lewis et al. |
| 5,911,872 A | 6/1999 | Lewis et al. |

(Continued)

OTHER PUBLICATIONS

A Highly Selective Acetylene Sensor A.M. Azad, S. Desikan, C.W. King, N.M. Bartos, N.A. Homann, C.S. Salupo, J.W. Harley International Meeting on Chemical Sensors Abstract, Jul. 13-16, 2008.*

(Continued)

*Primary Examiner* — Krishnan S Menon
*Assistant Examiner* — Dwan A Gerido
(74) *Attorney, Agent, or Firm* — Renner, Kenner; Arthur M. Reginelli

(57) ABSTRACT

A sensor for detecting the presence of unsaturated compounds, the sensor comprising: a semiconductor material doped with a metal halide in electrical connection with a monitoring device.

15 Claims, 3 Drawing Sheets

(56) References Cited

U.S. PATENT DOCUMENTS

| | | | |
|---|---|---|---|
| 6,033,601 | A | 3/2000 | Persaud et al. |
| 6,041,643 | A | 3/2000 | Stokes et al. |
| 6,093,308 | A | 7/2000 | Lewis et al. |
| 6,155,100 | A | 12/2000 | Stokes et al. |
| 6,182,500 | B1 | 2/2001 | Stokes et al. |
| 6,202,473 | B1 | 3/2001 | Stokes et al. |
| 6,289,716 | B1 | 9/2001 | Lindgren |
| 6,331,244 | B1 | 12/2001 | Lewis et al. |
| 6,890,715 | B1 | 5/2005 | Lewis et al. |
| 7,254,986 | B2 | 8/2007 | Stokes et al. |
| 7,367,217 | B2 | 5/2008 | Stokes et al. |
| 7,501,091 | B2 | 3/2009 | Munoz et al. |
| 2002/0081385 | A1* | 6/2002 | Kron et al. ............ 427/384 |
| 2004/0129565 | A1 | 7/2004 | Prohaska et al. |
| 2006/0034731 | A1 | 2/2006 | Lewis et al. |
| 2007/0062812 | A1 | 3/2007 | Weber et al. |
| 2008/0149499 | A1 | 6/2008 | Ding et al. |
| 2008/0217173 | A1 | 9/2008 | Varney et al. |
| 2009/0166197 | A1 | 7/2009 | Grincourt et al. |
| 2011/0124113 | A1* | 5/2011 | Azad et al. ............ 436/139 |
| 2012/0196379 | A1* | 8/2012 | Azad et al. ............ 436/142 |

OTHER PUBLICATIONS

Interaction of Acetylene with Films of the Transition Metals Iron, Nickel, and Palladium W. Alter, D. Borgmann, M. Stadelmann, M. Worn, and G. Wedler J. Am. Chem. Soc. 1994, 116, 10041-10049.*

New Adsorbents Based on Principles of Chemical Complexation: Monolayer-Dispersed Nickel for Acetylene Separation by pi Complexation. Ralph T. Yang and Robert Foldes Ind. Eng. Chem. Res 1996, 35, 1006-1011.*

Jordan, Larry R. and Hauser, Peter C., "Electrochemical Sensor for Acetylene", Anal. Chem., 1997, 69, pp. 2669-2672.

Pickrell, G., Peng, W., and Wang, A., "Random-hole Optical Fiber Evanescent-Wave Gas Sensing", Optics Letters, vol. 29, No. 13, 2004, pp. 1476-1478.

Maitlis, Peter M., "The Palladium(II)-Induced Oligomerization of Acetylenes: An Organometallic Detective Story", Accounts of Chemical Research, vol. 9, 1976, pp. 93-99.

Yarai, Atsushi and Nakanishi, Takuji, "Optical Fiber Gas Sensor Based on Thermal Lens Spectroscopy", Review of Scientific Instruments, vol. 75, No. 10, 2004, pp. 3237-3241.

Alter, W. et al., "Interaction of Acetylene with Films of the Transition Metals Iron, Nickel, and Palladium", J. Am. Chem. Soc., 116, 1994, pp. 10041-10049.

International Report on Patentability for technology related International Appl. No. PCT/US2010/057999 dated Feb. 14, 2012; 8 pages.

International Search Report for technology related International Appl. No. PCT/US2010/057999 dated Apr. 5, 2011; 3 pages.

Dutta et al., "Sensing of carbon monoxide gas in reducing environments", Sensors and Actuators B 84 (2002), pp. 189-213.

Lauque et al., "Highly sensitive and selective room temperature NH3 gas microsensor using an ionic conductor (CuBr) film", Analytica Chimica Acta 515 (2004), pp. 279-284.

Huang et al., "Anion Effects on the Adsorption of Acetylene by Nickel Halides", Langmuir 1999, 15, pp. 7647-7652.

Yang et al., "New Adsorbents Based on Principles of Chemical Complexation: Monolayer-Dispersed Nickel(II) for Acetylene Separation by pi-Complexation", Ind. Eng. Chem. Res. 1996, 35, pp. 1006-1011.

* cited by examiner

METHODS AND DEVICES FOR DETECTING UNSATURATED COMPOUNDS

This application claims the benefit of U.S. Provisional Application Ser. No. 61/490,395, filed May 26, 2011, which is incorporated herein by reference.

TECHNICAL FIELD

Embodiments of the invention are directed toward methods for detecting unsaturated compounds such as acetylene.

BACKGROUND ART

In many situations there is a need to detect the presence of small unsaturated molecules such as those including alkenylic or alkynylic unsaturation. As those skilled in the art appreciate, these small molecules are often gases at standard conditions, which are the conditions under which detection is often needed. While elaborate systems for detecting these compounds exist, there is often a need to detect these molecules in situations or environments where known systems are too cumbersome, too expensive, and/or simply inoperable.

There is, therefore, a need for new techniques and/or devices to detect small unsaturated molecules.

SUMMARY OF INVENTION

Embodiments of the present invention provide a method for detecting an unsaturated compound, the method comprising monitoring change in electrical properties of a substance that reacts or interacts with unsaturated compounds.

Further embodiments of the present invention provide a sensor for detecting acetylene gas comprising a substrate having a surface, electrodes in electrical communication with the surface, and a sensor layer formed of metal halide.

DETAILED DESCRIPTION OF THE ILLUSTRATIVE EMBODIMENTS

Figure 1:
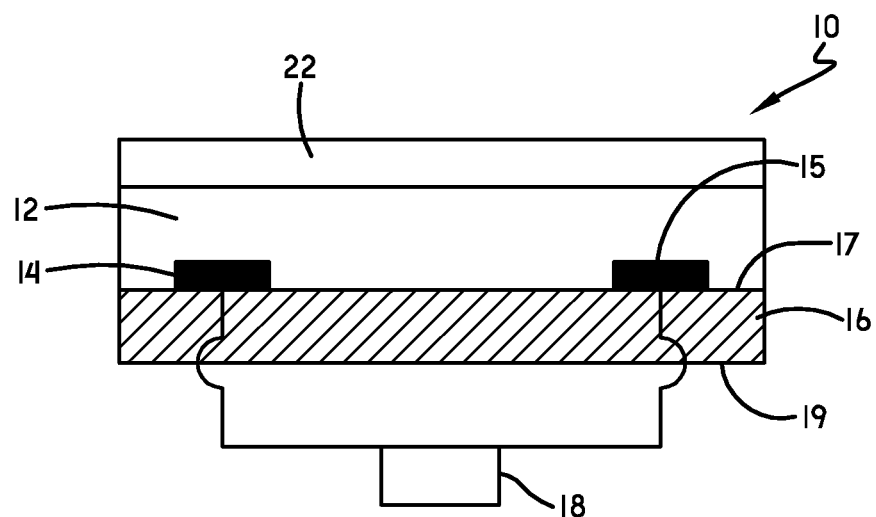
FIG. 1 cross-sectional view of a gas sensor device schematically connected to a detection circuit according to one or more embodiments of the invention.

Embodiments of the invention are based, at least in part, on the discovery that unsaturated compounds react or interact with certain substances and thereby alter the electrical properties of the substance. As a result, useful techniques for detecting the presence of unsaturated compounds are provided. In one or more embodiments, detection devices (e.g., sensors) are provided that operate, at least in part, based on the change in electrical properties caused by the interaction or reaction of unsaturated compounds with the substance.

Unsaturated Compounds

In one or more embodiments, unsaturated compounds include organic compounds including at least one double bond or at least one triple bond. In one or more embodiments, unsaturated compounds include hydrocarbons. In particular embodiments, the unsaturated compounds include alkenes (also known as olefins) such as, but not limited to, ethene, propene, 1-butene, 1-pentene, and 2-pentene. In other embodiments, the unsaturated compounds include alkynes such as, but not limited to, ethyne (also known as acetylene), propyne (also known as methylacetylene), butyne, and pentyne. In particular embodiments, the target unsaturated compound is acetylene. In one or more embodiments, unsaturated compounds include those compounds that include an alkenyl group. In these or other embodiments, unsaturated compounds include those compounds that include an alkynyl group. In one or more embodiments, the unsaturated compounds may be liquids at conditions of standard pressure and temperature. In other embodiments, the unsaturated compounds may be gases at conditions of standard pressure and temperature.

In particular embodiments, the unsaturated compounds may be characterized by having a relatively low molecular weight. For example, in one or more embodiments, the molecular weight of the unsaturated compounds may be less than 60 g/mole, in other embodiments less than 50 g/mole, in other embodiments less than 40 g/mole, and in other embodiments less than 30 g/mole.

Substance that Interacts with Unsaturated Compounds

In one or more embodiments, the interaction between the unsaturated compound and the substance that interacts with the unsaturated compound results in changes in the electrical properties of the substance. In one or more embodiments, the change in electrical properties may be manifested, for example, in a change in the conductivity (or resistivity) or capacitance of the substance. Without wishing to be bound by any particular theory, it is believed that the change in electrical properties is caused by it bonding through electrons between the unsaturated compound and the substance. Nonetheless, for purposes of this specification, the term interact may be used to describe the phenomena that exhibits, demonstrates, undergoes or gives rise to the change in electrical properties and therefore encompasses any interaction or reaction that may occur.

In one or more embodiments, the substance that interacts with unsaturated compounds is a transition metal compound, such as a transition metal salt. Useful transition metals include, but are not limited to, copper (I), copper (II), nickel (II), cobalt (II), iron (II), zinc (II), and silver (I). Useful salts of these transition metals include halides, such as, but not limited to, chlorides, bromides, and iodides, as well as nitrates. Exemplary transition metal compounds include copper (I) chloride, nickel (II) chloride, cobalt (II) chloride, iron (II) chloride, zinc (II) chloride, and silver nitrate ($AgNO_3$). In particular embodiments, the substance employed is copper (I) chloride. In other particular embodiments, the substance employed is nickel (II) chloride.

In particular embodiments, the purity of the substance (e.g. metal halide) impacts that ability of the substance to interact with the unsaturated compounds. Accordingly, in one or more embodiments, the purity of the metal halide (e.g. cuprous chloride) is at least 96%, in other embodiments at least 98%, and in other embodiments at least 99%. Stated another way, in one or more embodiments, the metal halide includes less than 5%, in other embodiments less than 3%, and in other embodiments 1% by weight impurity, which, for example, refers to the weight of non-cuprous chloride atoms or molecules in the molecular arrangement or crystal lattice of the cuprous chloride.

Advantageously, the change in electrical properties can be monitored. For example, a voltage can be applied across the substance and changes in the current across the substance can be monitored. Advantageously, it has been discovered that the change in electrical properties (e.g. resitivity) in the presence of the unsaturated compounds is proportional to the concentration of the unsaturated compounds in the environment in which detection of the unsaturated compounds takes place. In one or more embodiments, the resistivity of the substance decreases proportionally with the increasing concentration of acetylene within the environment in which the substance exists. Moreover, the reaction or interaction between the substance and the unsaturated compounds is reversible. In other words, the change in electrical properties can be reversed as concentration of unsaturated compounds in the environment in which a sensor is placed is reduced. For example, as a sensor is moved from an environment having higher concentration of unsaturated compound to an environment having lower concentration of unsaturated compound, the conductivity of the sensor layer will decrease proportionally to the change in concentration of unsaturated compounds. Likewise, as the sensor is moved from an environment having lower concentration of unsaturated compound to an environment having higher concentration of unsaturated compound, the conductivity of the sensor layer will increase proportionally to the change in concentration of unsaturated compounds.

In one or more embodiments, the substance that interacts with the unsaturated compound exhibits an initial resistance of at least 0.1 kiloohms, in other embodiments at least 1.0 kiloohm, and in other embodiments at least 10 kiloohms. In these or other embodiments, the initial resistance is less than 1,000 kiloohms, in other embodiments less than 500 kiloohms, and in other embodiments less than 100 kiloohms. In one or more embodiments, the change in resistivity of the substance based upon interaction with the unsaturated compound is at least 1%, in other embodiments at least 5%, and in other embodiments at least 10% at a concentration of 1 ppm of the unsaturated compound. In one or more embodiments, the substance that interacts with the unsaturated compound shows a change in electrical properties in the presence of the unsaturated compound at a temperature in the range of 20 to 130° C., in other embodiments from 50 to 120° C., and in other embodiments from 60 to 110° C.

In particular embodiments, the use of nickel (II) chloride has proven to be unexpectedly useful in the detection of acetylene. Advantageously, acetylene interacts with nickel (II) chloride, and the interaction or reaction unexpectedly alters the electrical properties of the nickel (II) chloride such that the change in electrical properties can be detected. Advantageously, the initial resistivity of nickel (II) chloride is in the range of about 10 to about 100 kiloohms (e.g., 20 to 80 kiloohms), and the change in resistivity is proportional to the concentration of acetylene. And, the nickel (II) chloride demonstrates a change in resistivity of about 10% at a concentration of 1 ppm acetylene. This change in resistivity can be easily monitored in view of the initial resistivity. Further, the change in resistivity of the nickel (II) chloride in the presence of acetylene has been found to be reversible and reliable at temperatures up to 120° C. (e.g., 100-110° C.).

Device for Detecting Unsaturated Compounds

A device for detecting unsaturated compounds according to one or more embodiments of the present invention can be generally described with reference to FIG. 1. As those skilled in the art will appreciate, FIG. 1, like other figures presented in this specification, is not drawn to scale and is primarily provided to illustrate the relationship of the various elements of the combinations presented.

The device 10 includes a substance 12 that reacts or interacts with unsaturated compounds and as a result exhibits a change in electrical properties as described above with respect to other embodiments or sub-embodiments of this invention. In particular embodiments, substance 12 is metal halide (e.g. cuprous chloride or nickel (II) chloride). In one or more embodiments, substance 12 is in the form of a continuous layer that allows electrons (i.e. a current) to travel across the layer; reference may simply be made to layer 12 or to sensor layer 12. The thickness of layer 12 can vary. For example, in particular embodiments, the thickness of layer 12 can be on the atomic level (e.g. the thickness may be one or more atoms thick) up to a thickness on the micron level (e.g. from 1 to 1000 microns).

In one or more embodiments, sensor layer 12 is disposed on at least a surface 17 of a substrate 16 and on at least a portion of first and second electrodes 14 and 15, which are thereby in electrical connection with sensor layer 12 and allow a voltage to be applied across sensor layer 12. As shown in FIG. 1, first and second electrodes may also be disposed on surface 17 of substrate 16. As those skilled in the art appreciate, these electrodes may be referred to as positive and negative electrodes (e.g. positive electrode 14 and negative electrode 15).

Substrate 16 may include or be formed from a non-conductive or semi-conductive material. In particular embodiments, substrate 16 is inert and non-conductive, where inert refers to the fact that the electrical properties of substrate 16 do not change as the result of any interaction with an unsaturated compound within the context of this specification. In these or other embodiments, substrate 16 does not interact with unsaturated compounds. Exemplary materials that may be used as substrate 16 include, without limitation, alumina ($Al_2O_3$) (e.g. high-density polycrystalline alumina), quartz ($SiO_2$), magnesia (MgO), or zirconia ($ZrO_2$).

In one or more embodiments, at least a second surface 19 of substrate 16 may be in contact with a heating device, such as a platinum resistance heater (not shown), as well as complementary detection and sensing devices, that can be used to heat and maintain the temperature of device 10 at a desired temperature.

As is generally known in the art, electrodes 14 and 15 may be fabricated from and therefore include any conductive material including those commonly employed in the art such as platinum, silver, and gold. Practice of the present invention is not limited by the number or type of electrodes employed. As those skilled in the art will appreciate, numerous electrode designs can be configured.

Figure 3:
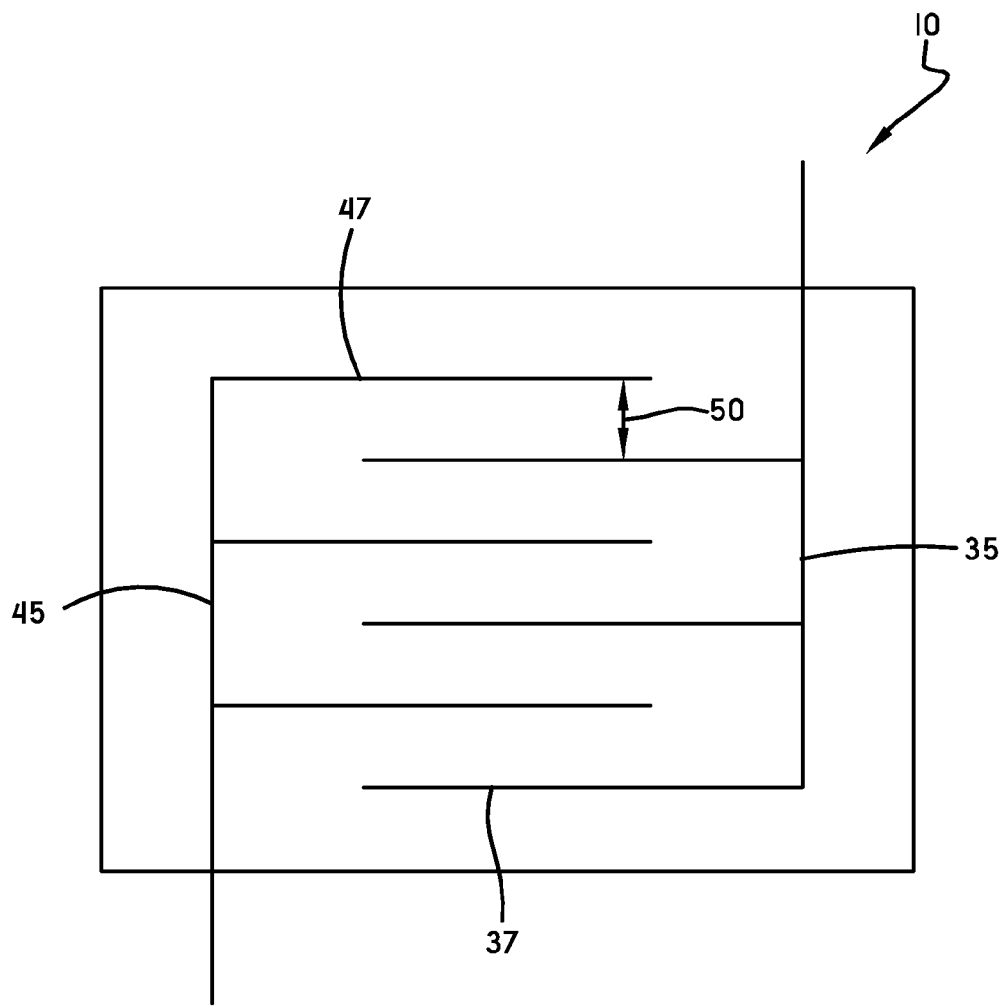
FIG. 3 is a schematic view of a gas sensor device according to one or more embodiments of the invention.

In one or more embodiments, electrodes 14 and 15 may include interdigitated electrodes (IDEs) 35 and 45 as generally shown in FIG. 3. IDEs are generally known in the art. Practice of the present invention is not necessarily limited by the selection of particular IDEs. As shown, the IDEs 35 and 45 may include interdigitated projections 37 and 47 respectively. Projections 37 and 47 may be spaced apart by gaps 50. As those skilled in the art will appreciate, practice of the present invention is not limited by the number of projections or the size of the gaps. These electrodes, in a manner consistent with that described above, include or are prepared from conductive material and are electrically connected with device or detection circuit 18, which may be accomplished through connection terminals (not shown) as know in the art.

In one or more embodiments, electrical detection device 18, which may also be referred to as a detection circuit, is in electrical connection with electrodes 14, 15. For example, detection device 18 may include a current meter. In one or more embodiments, electrical detection device 18 applies a voltage across layer 12 and monitors the change in electrical resistivity (or conductivity) across layer 12. Practice of the present invention is not limited by the selection of any particular electrical detection device 18 or devices (not shown). For example, electrical detection and monitoring may be provided by a single device or by two or more devices working in combination with each other (not shown). The voltage that can be applied across layer 12 may be in the form of alternating current (AC). As those skilled in the art appreciate, this AC can be rectified to DC, filtered, offset, and scaled to better detect changes in the electrical properties of layer 12. As is known in the art, detection circuit 18 may include any hardware and/or software necessary for carrying out the various detecting functions. In one or more embodiments, detection circuit 18 may include a visual display, such as an LCD display, or other predetermined audible, mechanical, or visual alerts or prompts generated by detection circuit 18 when sensor layer 12 reacts or interacts with the target unsaturated compound.

In one or more embodiments, device 10 may include optional permeable-protective layer 22, which may be simply referred to as protective layer 22 or protective coating 22. Protective layer 22 may be disposed directly on sensor layer 12 as shown, or it may be disposed on other intermediary layers disposed between sensor layer 12 and protective layer 22. In one or more embodiments, protective layer 22 includes or is formed from a material that is permeable to the unsaturated compound that is being detected and impermeable, or substantially impermeable, to other compounds or constituents in the environment that may deleteriously impact sensor layer 12 or the ability of sensor layer 12 to react or interact with the unsaturated compound that is being detected. For example, protective layer 22 may be impermeable to water or organic molecules that are larger than the unsaturated compound targeted for detection, while it is permeable to the unsaturated compound targeted for detection. In particular embodiments, protective layer 22 includes a hydrophobic coating.

Practice of the present invention is not necessarily limited by the thickness of protective layer 22. In particular embodiments, the thickness of protective layer 22 may be on the micron level; for example, the thickness of layer 22 may be from about 2 or 4 microns to about 100 or 500 microns (e.g., up to 10 or 50 microns).

In one or more embodiments, protective layer 22 includes or is formed from a fluorinated material. Fluorinated coatings and coating compositions (i.e. the composition from which the coating derives) that are useful for this purpose are known in the art. For example, fluorinated alkyl silanes or siloxanes, which are often referred to as FAS coatings, are known in the art as exemplified in U.S. Publ. Nos. 2002/0081385 and 2006/0229424, which are incorporated herein by reference.

In one or more embodiments, FAS compounds may include compounds where a silicon atom is bonded to four chemical groups. One or more of these groups contains fluorine and carbon atoms, and the remaining group(s) that may be attached to the silicon atoms may include alkyl, alkoxy, or halide group(s). Exemplary types of FAS compounds for use in protective layer 22 include, without limitation, $CF_3(CH_2)_2Si(OCH_3)_3$ [i.e., 3,3,3 trifluoropropyl)trimethoxysilane]; $CF_3(CF_2)_5(CH_2)_2Si(OCH_2CH_3)_3$ [i.e., tridecafluoro-1,1,2,2-tetrahydrooctyl-1-triethoxysilane]; $CF_3(CH_2)_2SiCl_3$; $CF_3(CF_2)_5(CH_2)_2SiCl_3$; $CF_3(CF_2)_7(CH_2)_2Si(OCH_3)_3$; $CF_3(CF_2)_5(CH_2)_2Si(OCH_3)_3$; $CF_3(CF_2)_7(CH_2)_2SiCl_3$; $CF_3(CF_2)_7(CH_2)_2SiCH_3Cl_2$; and/or $CF_3(CF_2)_7(CH_2)_2SiCH_3(OCH_3)_2$. These FAS material may be used either alone or in any suitable combination for protective layer 22. At least partial hydrolyzed versions (hydrolysate) of any of these compounds may also be used.

As noted above, the detection devices of this invention, such as device 10, may include multiple protective layers (not shown). Each protective layer should be permeable to the unsaturated compound or compounds being targeted for detection, and thereby allow the target unsaturated compounds to contact sensor layer 12. Each of the one or more protective layers, however, may be selectively permeable or impermeable to other constituents that may come into contact with device 10 (i.e. are present in the environment where the target unsaturated compounds are sought to be detected).

Figure 2:
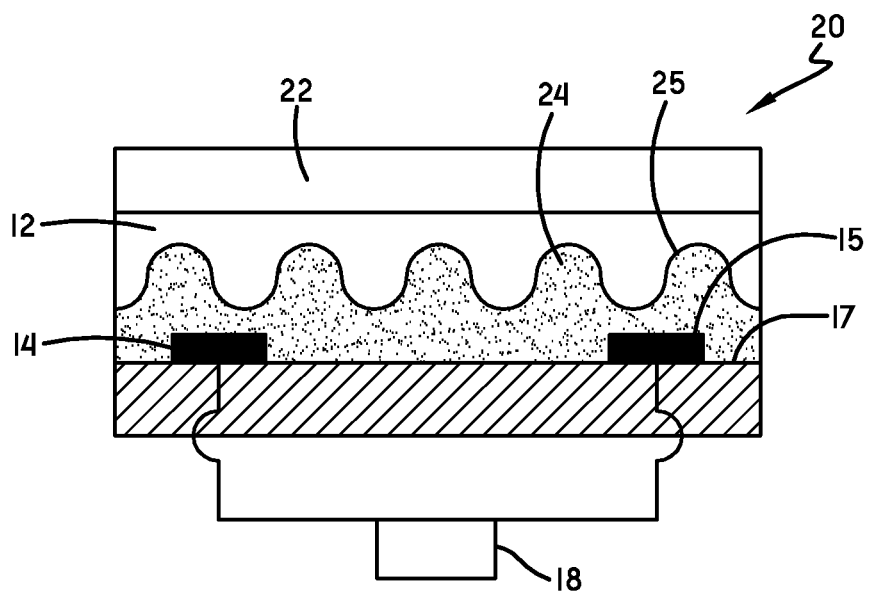
FIG. 2 cross-sectional view of a gas sensor device schematically connected to a detection circuit according to one or more embodiments of the invention.

Other embodiments of devices of the present invention may be described with reference to FIG. 2. As shown, detection device 20 includes sensor layer 12, first and second electrodes 14 and 15, substrate 16, electrical detection device 18, and optional protective layer 22, which may be consistent with the description provided above. In addition, detection device 20 may include optional support layer 24, which may also be referred to as matrix 24. Support layer 24 may be disposed on first surface 17 of substrate 16 and on at least a portion of electrodes 14 and 15. Sensor layer 12 may then be disposed on first surface 25 of semi-conductor layer 24. As a result of this arrangement, electrodes 14 and 15 are in electrical contact or communication with each other through sensor layer 12 and optionally through matrix 24; in other words a voltage can be applied across sensor layer 12 between electrodes 14 and 15, and optionally also across support 24 between electrodes 14 and 15.

In one or more embodiments, support layer 24 is porous and/or has a degree of surface roughness. In one or more embodiments, support layer 24 is porous or partially porous with respect to the target unsaturated compound. As a result, the porosity, partial porosity, and/or surface roughness, at least first surface 25 of support layer 24 has increased surface area and may therefore provide increased surface area to sensor layer 12, which is disposed on surface 25.

In one or more embodiments, the porosity of the support layer yields a structure that can be described as a doped or impregnated porous material; i.e., the support (e.g. semiconductor) is doped with the sensing material (e.g. nickel (ii) chloride). Without wishing to be bound by any particular theory, it is believed that the sensing material is dispersed throughout the matrix of the support rather than forming a layer over the support.

In one or embodiments, support or matrix layer 24 is a semi-conductor, and therefore layer 24 may also be referred to, in certain embodiments, as semi-conductor layer 24. Semi-conductor layer may be formed from and therefore include a metal oxide such as, without limitation, titanium dioxide ($TiO_2$ or Ti(IV) oxide or titania), tin dioxide ($SnO_2$ or Sn(IV) oxide), zinc oxide (ZnO or Zn(II) oxide), molybdenum oxide ($MoO_3$ or Mo(VI) oxide), tungsten oxide ($WO_3$ or W(VI) oxide), and mixtures of two or more of these compounds. For example, a mixture of titanium dioxide and tin dioxide may be employed; in particular embodiments, the ratio of titanium dioxide to tin dioxide may continuously range from about 100:1 to about 1:100.

The thickness of support layer 24 can vary. For example, in particular embodiments, the thickness of layer 24 can be on the atomic level (e.g. the thickness may be one or more atoms thick) up to a thickness on the micron level (e.g. from 1 to 1000 microns).

In these or other embodiments, any relationship that may exist between the sensor layer 12 and the semi-conductor layer 24 may be expressed in terms of the weight of the sensor material as a ratio to the weight of the semi-conductor material present in any given unit of area. For example, the weight/weight ratio of sensor material to semi-conductive material is from about 0.02 to about 100.

Figure 4:
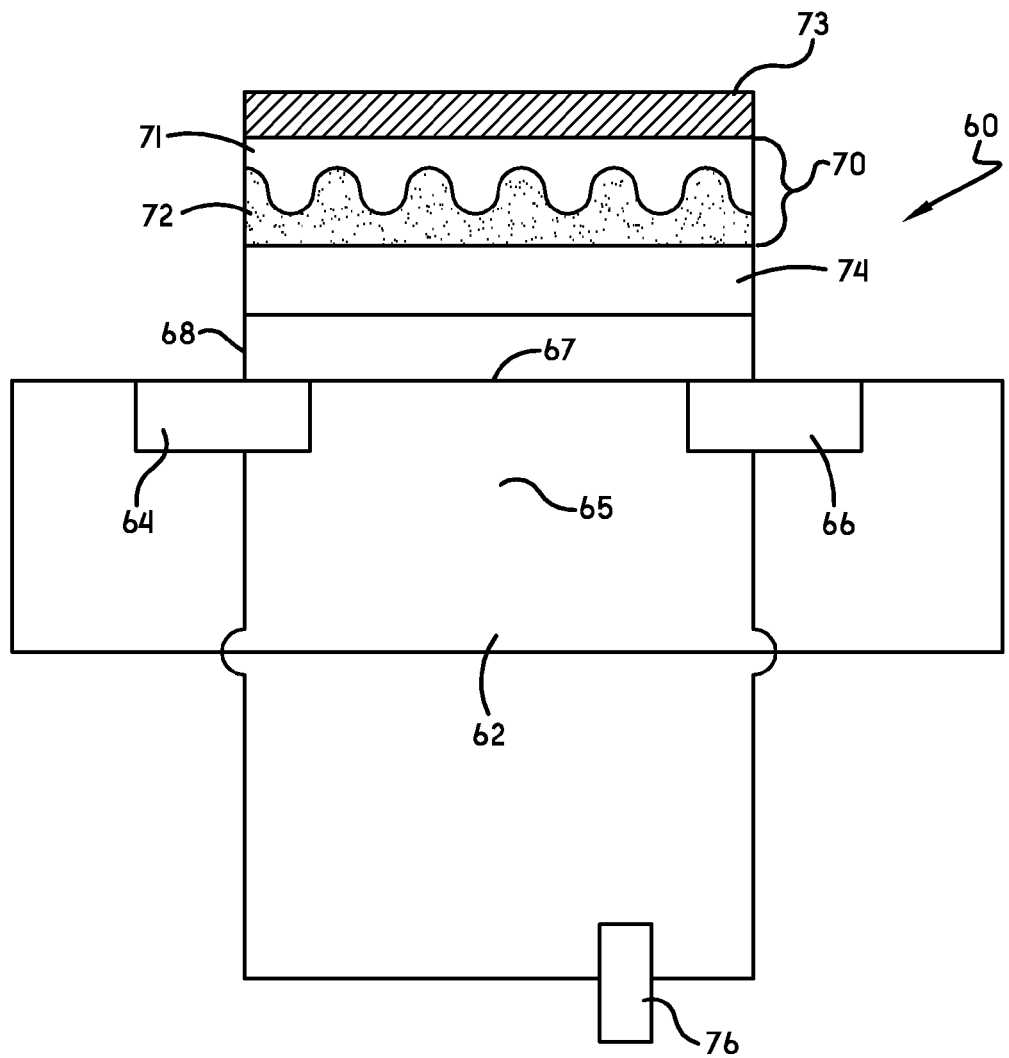
FIG. 4 is a schematic view of an IGFET-type device of the present invention.

In one or more embodiments, the sensor devices of this invention can be fabricated into an insulated-gate field-effect transistor (IGFET) as shown in FIG. 4. Transistor 60 includes a semiconductor substrate 62, a source region 64, and a drain region 66. Source region 64 is spaced apart from drain region 66, and both may be located at or near one surface 67 of substrate 62. The region of substrate 62 between source 64 and drain 66 is called the channel 65. A gate insulator 68, which may include a thin layer of insulating material, covers the surface 67 of channel 65. A gate electrode 70, which is a sensor layer within the context of this invention (e.g. metal halide layer), is disposed on and covers gate insulator 68. Gate electrode 70 includes a sensor substance 71 (e.g. metal halide) and optional support material (e.g. $TiO_2$) 72. In one or more embodiments, gate electrode 70 may also include a conductive layer disposed between gate insulator 68 and gate electrode 70. In those embodiments where the device includes conductive layer 74, the device may be referred to as a metal insulator semiconductor (MIS). The IGFET devices of this invention may also include an optional protective layer 73.

When gate electrode 70 (e.g. metal halide sensor layer) is exposed to an unsaturated compound (e.g. acetylene), the electric field in gate insulator 68 is modified. The electric field attracts or repels charge carriers, electrons or holes, in adjacent semiconductor material 62 thereby changing the conductance of channel 65. The change in conductance of channel 65 is related to the concentration of unsaturated compound interacting with sensor substance 71 and can be measured by a current meter 76 connected in series with a potential source, source region 64, and drain region 66.

Method of Fabricating Device

While practice of the present invention is not necessarily limited by the method used to produce the device of one or more embodiments of the present invention, the following method has been found to be advantageous. An inert substrate, such as a thin plate or wafer of dense (~100%) crystalline α-alumina, can be commercially obtained and may be optionally polished to provide at least one relatively smooth surface. A pair or multitude of electrodes, such as IDEs, can be placed on a surface (optionally a polished surface) of the alumina substrate by employing techniques known in the art of photolithography.

The substance that can interact with an unsaturated compound may then be deposited onto at least a portion of the substrate and onto at least a portion of each of the electrodes. In other embodiments, one or more semiconductor layers are first deposited onto at least a portion of the substrate and onto at least a portion of each of the electrodes, and then the substance that can react or interact with an unsaturated compound may then be deposited onto the at least a portion of the semiconductor layer.

In either event, the substance that can interact with an unsaturated compound may be deposited by using the following technique. In one embodiment, where cuprous chloride is employed, cuprous chloride may be commercially obtained at purity levels that are useful for practicing the present invention (e.g. 99%+). Where grades are obtained that include greater levels of impurities, or where further purification is desired, cuprous chloride may be further purified using techniques known in the art. For example, the cuprous chloride can be dissolved in concentrated hydrochloric acid, which will leave impurities, such as copper-II (cupric chloride) compounds undissolved, and allow for separation by using techniques such vacuum filtration; the cuprous chloride can then be precipitated out using copious amounts of water and dried using glacial acetic acid and optional further drying in a vacuum oven.

The cuprous chloride can be dissolved in appropriate solvents, such as acetonitrile, to form a solution that can be deposited onto at least a portion of the substrate and onto at least a portion of the each of the electrodes, or in other embodiments, onto at least a portion of the semiconductor layer and onto at least a portion of the each of the electrodes. The substrate can be heated (e.g. up to about 60-65° C.) when the solution of cuprous chloride is applied, or it may be subsequently heated to drive off or evaporate the solvent.

In those embodiments where nickel (II) chloride is employed, the nickel chloride can be dissolved in appropriate solvents, such as water, acetonitrile or a mixture of the two, to form a solution that can be deposited onto at least a portion of the substrate and onto at least a portion of each of the electrodes, or in other embodiments, onto at least a portion of the semiconductor layer and onto at least a portion of the electrodes. The substrate can be heated when the solution of nickel chloride is applied to drive off the solvent, preferably above the vaporization temperature of the solution (e.g. from about 100° C.-150° C. for an acetonitrile, water mixture) for quick evaporation and dispersion of the nickel chloride.

Where the device includes a semi-conductor layer, such as titanium dioxide or tin oxide or other suitable oxides mention above, the semiconductor layer may be formed from a slurry containing the metal oxide that is deposited on the substrate, and at least a portion of the electrodes, and subsequently fired to obtain a porous or partially porous film with some surface roughness. For example, titanium oxide powder that is at least about 99.5% pure can be commercially obtained and sieved to obtain a desirable particle size. In one or more embodiments, the metal oxide is sieved or otherwise separated to provide particles having a particle size of less than 200 μm, in other embodiments less than 40 μm, or in other embodiments less than 1 μm. The sieved powder can be formed into a slurry using an appropriate liquid vehicle such as 2-propanol. The slurry may then be applied to the target surface using known techniques (e.g. brushing or spraying), allowed to dry slowly in an air oven (e.g. overnight at 70° C.) and fired at appropriate temperatures for sufficient time (e.g. 700° C. for approximately 2 hours) to achieve a desired porous semiconductor layer.

The sensing layer can then be formed on the porous semiconductor layer by applying the solution (e.g. cuprous chloride in acetonitrile) described above to the surface of the semiconductor layer.

In one or more embodiments, the solution of the cuprous chloride is prepared and applied so as to deliver from about 1 microgram to about 200 micrograms, or in other embodiments from about 5 micrograms to about 50 micrograms, cuprous chloride per square mm of the substrate or semiconductor layer.

After the sensing material is applied to the substrate or semiconductor material and appropriately dried, it may be desirable to precondition the device. This may be accomplished by subjecting the device to an energy source. For example, the device can be heated in an oven under appropriate conditions. In other embodiments, an alternating current can be applied across the terminals (e.g. a 1-volt peak voltage at a frequency of between 10-100 Hz, although A.C. signals with other voltage magnitudes and frequencies may be used); this voltage may be applied for extended periods of time (e.g. 6 hours).

Protective layer(s) can be applied to the device by using known techniques for applying these coatings. For example, solutions of FAS coatings can be applied by using known techniques (e.g. brushing or spraying), and the solvent within the solution can be driven off using known techniques (e.g. heat and/or vacuum). The protective layer can be applied before or after preconditioning the device.

Packaging

As those skilled in the art appreciate, the various other sensor configurations can incorporate the sensor layer or sensor substance contemplated by this invention. Moreover, these various devices can be packaged or assembled within various packages known in the art. For example, and without limitation, these devices can be assembled with dual in-line packages (DIPs), surface mount packages (SMPs), and metal can packages (TO-type).

Industrial Applicability

In one or more embodiments, the techniques and devices of the present invention can advantageously be used to detect a number of unsaturated compounds in diverse environments. For example, where the unsaturated compound is in the gaseous state, the techniques and detectors of this invention can be used in liquid or gaseous environments. In other words, gaseous unsaturated compounds contained in a mixture of gases can be detected where the mixture of gases is in contact with the sensor. Or, unsaturated gaseous compounds dissolved in a liquid can be detected where the liquid is in contact with the sensor.

In particular embodiments, the sensors of the present invention are employed to detect the presence of acetylene in oil-filled electrical equipment such as power transformers. In these embodiments, the sensor can be placed in contact with the fluids contained in the electrical equipment (e.g. power transformer). A voltage (e.g. about 1 volt) can be applied across the sensor layer and/or semiconductor layer. In one or more embodiments, the sensing device can optionally be heated (e.g. to a temperature of about 100° C.). Using known techniques, a baseline voltage transmission can be determined for the device in the absence of acetylene within the transformer, which represents a degree of resistivity (or conductivity) across the device. This degree of conductivity can be continuously or intermittently monitored and compared to the base line. As acetylene is formed within the transformer and the concentration of the acetylene reaches concentrations that are detectable by the sensor, the conductivity of the sensor changes as the acetylene reacts or interacts with the sensor layer. The change in conductivity can be recorded on site at the transformer or communicated electronically to a location remote from the transformer.

In other particular embodiments, the sensors of the present invention are employed to detect the presence of acetylene or ethylene in food applications including, but not limited to, food ripening processes and food storage facilities.

Although the present invention has been described in considerable detail with reference to certain embodiments, other embodiments are possible. Therefore, the spirit and scope of the appended claims should not be limited to the description of the embodiments contained herein.

What is claimed is:

1. A method for detecting an unsaturated compound, the method comprising:
   (i) providing a device including
      (a) a substrate having a surface, where the substrate is non-conductive and the electrical properties of the substrate do not change as a result of any interaction with unsaturated compounds;
      (b) electrodes;
      (c) a semiconductor layer that is at least partially porous;
      (d) a sensor layer formed of nickel (II) chloride deposited on said support; and
      (e) a protective layer on said sensor layer, where the semiconductor layer is doped with the nickel (II) chloride;
   (ii) applying a voltage across the sensor layer between said electrodes; and
   (iii) detecting the presence of alkynes or alkenes by monitoring change in electrical properties of the sensor layer as the sensor layer interacts with the alkynes or alkenes.

2. The method of claim 1, where the unsaturated compound is acetylene.

3. The method of claim 1, where the unsaturated compound is ethylene.

4. The method of claim 1, where the change in electrical properties is proportional to the amount of alkynes or alkenes present.

5. The method of claim 1, where the method includes placing the device into a power transformer while protecting the nickel (II) chloride from liquids contained within the power transformer.

6. The method of claim 1, where the change in electrical properties results from $\pi$ bonding between the unsaturated compound and the nickel (II) chloride.

7. A method for detecting an unsaturated compound, the method comprising:
   (i) placing a sensor in an environment having the potential for unsaturated compounds, where the sensor includes nickel (II) chloride and an at least partially porous semiconductor and an electrical detection device in electrical communication with the nickel (II) chloride, where the semiconductor is doped with the nickel (II) chloride; and
   (ii) monitoring the change in electrical properties of the nickel (II) chloride via the electrical detection device to thereby determine the presence of unsaturated compounds, where the unsaturated compounds are selected from the group consisting of alkynes and alkenes, where the sensor further includes a protective layer that is permeable to the unsaturated compounds and is impermeable or substantially impermeable to organic molecules that are larger than the unsaturated compounds.

8. The method of claim 7, where said step of placing the sensor in an environment includes placing the sensor in contact with fluids contained within a power transformer.

9. The method of claim 7, where the unsaturated compound is acetylene.

10. The method of claim 7, where the unsaturated compound is ethylene.

11. The method of claim 7, where the protective layer is impermeable or substantially impermeable to water.

12. A sensor for detecting acetylene gas comprising:
   (i) a substrate having a surface, where the substrate is non-conductive and the electrical properties of the substrate do not change as a result of any interaction with unsaturated compounds;
   (ii) electrodes;
   (iii) a semiconductor layer that is at least partially porous;
   (iv) a sensor layer formed of nickel (II) chloride deposited on said support; and
   (v) a protective layer on said sensor layer, where the semiconductor layer is doped with the nickel (II) chloride.

13. The sensor of claim 12, where said electrodes are sandwiched between said support and said substrate.

14. A sensor for detecting the presence of unsaturated compounds, the sensor comprising:
- a semiconductor material doped with a nickel (II) chloride in electrical connection with a monitoring device, and where the semiconductor material is selected from the group consisting of titanium dioxide ($TiO_2$ or Ti(IV) oxide or titania), tin dioxide ($SnO_2$ or Sn(IV) oxide), zinc oxide (ZnO or Zn(II) oxide), molybdenum oxide ($MoO_3$ or Mo(VI) oxide), tungsten oxide ($WO_3$ or W(VI) oxide), and mixtures of two or more of these compounds.

15. The sensor of claim 1, where the semiconductor is selected from the group consisting of titanium dioxide ($TiO_2$ or Ti(IV) oxide or titania), tin dioxide ($SnO_2$ or Sn(IV) oxide), zinc oxide (ZnO or Zn(II) oxide), molybdenum oxide ($MoO_3$ or Mo(VI) oxide), tungsten oxide ($WO_3$ or W(VI) oxide), and mixtures of two or more of these compounds.

\* \* \* \* \*